United States Patent [19]

Tann et al.

[11] Patent Number: 5,539,121
[45] Date of Patent: Jul. 23, 1996

[54] 2-FORMYLMERCAPTOBENZOTHIAZOLE

[75] Inventors: Chou-Hong Tann, Berkeley Heights; Tiruvettipuram K. Thiruvengadam, Edison; John S. Chiu, Parsippany; Cesar Colon, Rahway; Michael D. Green, Paterson, all of N.J.

[73] Assignee: Schering Corporation, Kenilworth, N.J.

[21] Appl. No.: 442,084

[22] Filed: May 16, 1995

Related U.S. Application Data

[62] Division of Ser. No. 138,558, Oct. 15, 1993, Pat. No. 5,442,047, which is a continuation of Ser. No. 777,385, Dec. 4, 1991, abandoned, which is a continuation of PCT/US90/03328, Jun. 19, 1990, which is a continuation of Ser. No. 369,578, Jun. 21, 1989, abandoned.

[51] Int. Cl.$^6$ .................................................. C07D 417/00
[52] U.S. Cl. .......................... 548/162; 548/165; 536/13.6
[58] Field of Search .................................... 548/162, 165

[56] References Cited

U.S. PATENT DOCUMENTS

| | | | |
|---|---|---|---|
| 3,932,427 | 1/1976 | Durant et al. | 424/263 |
| 4,136,254 | 1/1979 | Nagabhushan et al. | 536/10 |
| 4,230,847 | 10/1980 | Nagabhushan et al. | 536/10 |
| 4,242,331 | 12/1980 | Gasc et al. | 424/180 |
| 4,268,664 | 5/1981 | Umezawa et al. | 536/10 |
| 4,283,528 | 8/1981 | Daniels et al. | 536/17 R |
| 4,297,485 | 10/1981 | Umezawa et al. | 536/10 |
| 4,347,354 | 8/1982 | Cron et al. | 536/10 |
| 4,614,601 | 9/1986 | Sekimoto et al. | 536/88 |

FOREIGN PATENT DOCUMENTS 0156771  10/1985  European Pat. Off. ....... C07D 501/06

OTHER PUBLICATIONS

Tsuchiya, et al. Tetrahedron Letters No. 51, pp. 4951–4954 (1979).
Thomas, et al. Tetrahedron Letters, vol. 21, pp. 4981–4984 (1980).
Greenstein, et al. Chemistry of the Amino Acids, vol. 2, John Wiley & Sons, pp. 920–921.
Greene Protective Groups in Organic Synthesis, John Wiley & Sons (1981) p. 52.

*Primary Examiner*—Elli Peselev
*Attorney, Agent, or Firm*—Warrick E. Lee, Jr.

[57] ABSTRACT

There is disclosed a novel formylating agent, 2-formylmercaptobenzothiazole.

1 Claim, No Drawings

2-FORMYLMERCAPTOBENZOTHIAZOLE

This is a Divisional of U.S. application Ser. No. 08/138,558 filed Oct. 15, 1993, now U.S. Pat. No. 5,442,047, which in turn is a continuation of U.S. application Ser. No. 07/777,385 filed Dec. 4, 1991, now abandoned, which was the United States national application corresponding to International Application No. PCT/US90/03328 filed Jun. 19, 1990 and designating the United States, which PCT application is in turn a continuation of U.S. application Ser. No. 369,578 filed Jun. 21, 1989, now abandoned, the benefit of which applications is claimed pursuant to 35 U.S.C. 120, 363, and 365(c).

This invention relates to a novel process for converting gentamicin B to isepamicin, 1-N-[(S)-3-amino-2-hydroxypropionyl] gentamicin B and to a novel formylating agent, 2-formylmercaptobenzothiazole, useful in the process.

More particularly, this invention relates to a process for converting gentamicin B to 3,6'-di-N-formylgentamicin B by using 2-formylmercaptobenzothiazole, acylation of the 1-amino group with an (S)-isoserine derivative, followed by removal of the protecting groups under conditions which result in high yields of the desired product.

Isepamicin, which has the formula

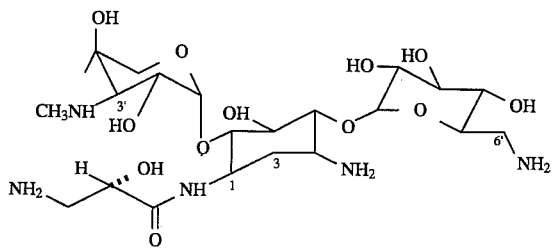

is a known aminoglycoside antibiotic. The preparation of this compound from gentamicin B is described in U.S. Pat. No. 4,230,847. The process described in the patent involves forming 3,6'-di-N-benzyloxycarbonyl gentamicin B by reacting a cuptic-nickel (II) salt complex of gentamicin B with N-benzyloxycarbonyloxy-phthalimide and then reacting the intermediate compound with N-(S-3-benzyloxycarbonylamino-2-hydroxypropionyloxy) succinimide. The benzyloxycarbonyl protecting groups were removed from the resulting material by catalytic hydrogenation over palladium-on-carbon to produce isepamicin in 60% yield from the intermediate starting material.

Tsuchiya, et al., Tetrahedron Letters No. 51, pp 4951–4954 (1979), describe a complex multistep process for the protection of the 3,3",6'-amino groups in Kanamycin A comprising zinc acetate chelation, 3,6'-N-bisbenzyloxycarbonylation, zinc removal, carbonate formation, and finally trifluoroacetylation of the 3"-amino group. The 3,3",6'-N-triblocked Kanamycin A so produced is then acylated at the free C-1 amino group using an active ester of 1-N-[(S)-4-benzyloxycarbonylamino]-2-hydroxybutyric acid. Finally the resulting product is subjected to a 2-part deprotection scheme to give Amikacin. A similar sequence is also described for the conversion of dibekacin to its 1-N-[(S)-4-amino-2-hydroxybutyryl] derivative. No reference to the use of this process for the selective acylation of other aminoglycosides was disclosed. The Tsuchiya et al. process sequence is cumbersome involving both trifluoroacetylation and benzyloxycarbonylation in the protection steps and requiring both aminolysis and hydrogenolysis in the deprotection steps. These steps render the process commercially unattractive both in the sense of operating costs and capital requirements for implementation. Furthermore, in our hands, and contrary to the implications in the Tsuchiya et al. process description, zinc acetate chelation does not invariably lead to selective 3,6'-diblockade in aminoglycosides other than Kanamycin and dibekacin. Thus, unexpectedly, the zinc acetate chelation of gentamicin B followed by acylation with formylimidazole leads primarily to 1,6'-N-diformylation and not 3,6'-diformylation. Again acylation of this same gentamicin B zinc acetate chelate with a different formylating agent, formylacetic mixed anhydride, gives rise, in addition to the desired 3,6'-N-diformyl-gentamicin B, to undesired levels of acetylated gentamicin B products. To underline the difficulty of prediction, formyl p-nitrobenzoic mixed anhydride proved insufficiently reactive to be useful in the formylation of gentamicin. B zinc acetate chelate, whereas use of formyl p-anisic mixed anhydride afforded excellent yields of the desired 3,6'-diformyl gentamicin B, contaminated with minor amounts of anisoyl impurities.

Use of metal acetates, for example, zinc acetate and the like, give rise to small amounts of undesirable by-products, for example N-acetyl derivatives, which are difficult to remove and decrease the yield of desired product.

The formylation of aminoglycosides has been previously described by Thomas et al., Tetrahedron Letters, Vol. 21, pp 4981–4984 (1980) in connection with the preparation of 1-N-alkylated Kanamycin antibiotics. However, Thomas et al. do not teach the value of formylation as an amine-protecting group in producing 1-N-acylated aminoglycosides. Nor is this point recognized in any other aminoglycoside literature. Instead, the literature describes the use of such as trifluoroacetyl, trichloroacetyl, and phthaloyl groups for the protection of amine groups and teaches that the aminolysis or hydrazinolysis of such groups can be carried out without materially affecting certain other N-acyl groups which may be present on the molecule. In short the selective aqueous base hydrolysis of formyl groups from 3,6'-N-formylated-1-N-acylated aminoglycosides is unprecedented.

We have now found that a novel formylating agent 2-formylmercaptobenzothiazole of formula II,

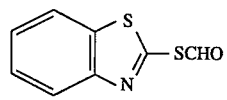

can selectively formylate the 3, 6'-amino groups of the gentamicin B zinc chelate. Moreover, the procedure of this invention result in a high yield if one uses a different zinc salt, such as zinc pivaloate, to avoid formation of undesirable by-products. Furthermore, we have found that a 3,6'-N-diformyl gentamicin B obtained, by removing zinc from the chelate, can be selectively acylated with N-formyl-(S)-isoserine active ester only at the C-1 amino group without separate protection of the C-3" methylamino group as in the Tsuchiya et al. procedure. Finally, we have found that all formyl groups can be removed from the resulting 3,6'-N-diformyl-1-N-[N-formyl-(S)-isoserinoyl]-gentamicin B by aqueous base hydrolysis in high yield without removing the desired isoserine side chain.

SUMMARY OF THE INVENTION

This invention relates to an improved multistep process for converting gentamicin B to isepamicin in high yields.

The process of this invention comprises (a) reacting gentamicin B with a chelating agent and then with 2-formylmercaptobenzothiazole capable of selectively introducing formyl groups in gentamicin B to form 3,6'-di-N-formylgentamicin B.
(b) acylating the 1-amino group of 3,6'-di-N-formylgentamicin B with an activated N-acyl protected (S)-isoserine compound;
(c) removing all protecting groups; and
(d) isolating isepamicin.

DETAILED DESCRIPTION OF THE INVENTION

The intermediate compound, 3,6'-di-N-formylgentamicin B, is prepared by reacting a divalent metal salt complex of gentamicin B with 2-formylmercaptobenzothiazole to introduce formyl protecting groups at the 3,6'-positions. The metal salt complex is prepared using methods disclosed in U.S. Pat. No. 4,136,254 and Thomas, et al., Tetrahedron Letter, Vol. 21, 4981–4984 (1980).

The reaction scheme for preparing 3,6'-di-N-formylgentamicin B (III) is set forth below:

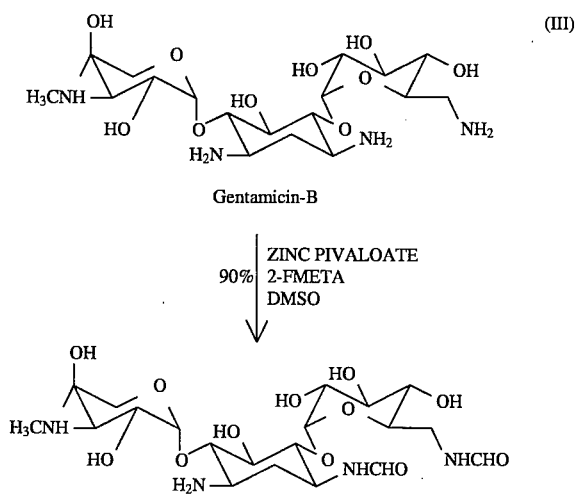

Transition metal salts useful as complexing agents in the process of this invention include such divalent salts as copper (II), nickel (II), cobalt (II), cadmium (II) and zinc (II) as well as mixtures thereof. The divalent metal salts are salts of organic acids, preferably organic acids such as formic, acetic, propionic, pivalic and benzoic acid. Preferred divalent metal salts include pivaloate salts of zinc (II) and cobalt (II). Of particular use is zinc (II) pivaloate.

The formation of the divalent salt complex of gentamicin B is carried out in an inert organic solvent. Preferred organic solvents are for example, dimethylsulfoxide, dimethylformamide, dimethylacetamide, methylene chloride, toluene, ethyl acetate and mixtures thereof.

In preparing the divalent salt complex of gentamicin B, it has been found advantageous to employ from about 1.5–4.5 moles of the divalent salt, for example zinc (II), per mole of gentamicin B. The preferred molar ratio of reagents is about 2.7–3.5 moles of divalent salt per mole of gentamicin B.

The divalent salt complex of gentamicin B is reacted with 2-formylmercaptobenzothiazole which introduces a formyl protecting group at both the 3 and 6'-amino groups.

The molar quantity of 2-formylmercaptobenzothiazole is usually 2–3 to 1 of the molar quantity of the divalent salt complex of gentamicin B. The preferred molar quantity is 2.5 to 1.

Formylation of this divalent salt complex of gentamicin B is carried out at a temperature of from 0° C. to 40° C., preferably from 20° C. to 30° C.

The formylation reaction of the divalent salt complex of gentamicin B is conveniently carried out in an organic solvent or a mixture of organic solvents. Organic solvents that can be utilized in this reaction include dipolar aprotic organic solvents, for example, dimethylsulfoxide, dimethyl formamide, dimethyl acetamide, and the like. It has also been found advantageous to employ mixtures of a dipolar aprotic organic solvent with an inert organic solvent, for example, toluene, ethyl acetate, 1,2-dimethoxyethane, tetrahydrofuran, acetonitrile, methylene chloride, and the like. A preferred mixture of solvents is dimethyl sulfoxide with either methylene chloride or ethyl acetate.

While all prior processes require the use of a precipitating agent or a procedure to remove the divalent metal salt cation, the use of 2-formylmercaptobenzothiazole and zinc allows for an extractive removal of the zinc 2-mercaptobenzothiazole salt in the organic solvent layer.

The aqueous solution comprises 3, 6'-di-N-formylgentamicin B in a yield of approximately 90–95%. The product can be isolated and purified by conventional methods such as ion exchange chromatography.

Introduction of the (S)-isoserine side-chain at the 1-amino group of 3,6'-di-N-formylgentamicin B is carried out by means of in-situ active ester formation of the N-protected-(S)-isoserine with an activating reagent in the presence of dicyclohexylcarbodiimide according to the following reaction scheme:

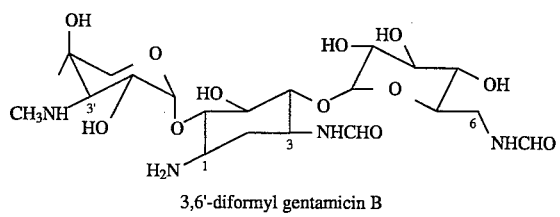

3,6'-diformyl gentamicin B          III

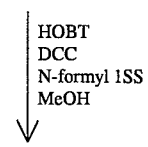

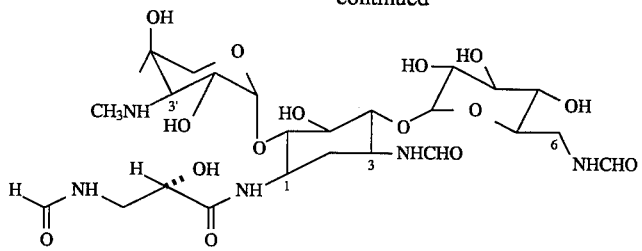

IV

N-Protected -(S)-isoserine compounds that are useful in the process of this invention are hose wherein the amino group of -(S)-isoserine is protected with an acyl group which can be easily removed under conditions which remove formyl protecting groups and which will not affect other portions of the molecule. Acyl protecting groups which can be easily removed under mild basic conditions or with hydrazine are utilized in the process. Examples of N-acyl protecting groups which are easily removed under mild basic conditions include formyl, trichloroacetyl and trifluoroacetyl. Examples of N-acyl protecting groups which are easily removed by hydrazine include phthaloyl and succinoyl. The preferred N-acyl protecting group for the isoserine compound is the formyl group.

N-Protected isoserine compounds that are useful in the process of this invention include N-formyl-(S)-isoserine, N-phthaloyl-(S)-isoserine; N-trichloroacetyl-(S)-isoserine, and N-trifluoroacetyl-(S)-isoserine. The preferred N-protected isoserine compound is N-formyl-(S)-isoserine.

Active esters of N-protected-(S)-isoserine are prepared by reacting the isoserine compound with a compound such as N-hydroxybenzotriazole, N-hydroxy succinimide, imidazole, N-hydroxyphthalimide, N-hydroxy-5-norbornene-2,3-dicarboximide and the like, in the presence of a coupling agent such as dicyclohexyl-carbodiimide.

The reaction of N-protected -(S)-isoserine with 3,6'-di-N-formyl gentamicin B is carried out at temperatures between 0° C. and 40° C., preferably at about room temperature, in a solvent. Examples of solvents which can be employed in the process of this invention include protic organic solvents, for example alcohols, such as methanol, ethanol, propanol and the like; mixtures of water and alcohol, such as aqueous methanol, aqueous ethanol, and the like; aprotic solvents, such as dimethyl formamide, dioxane, methylene chloride. A preferred solvent is aqueous methanol.

The compound obtained by reacting N-formylisoserine with 3,6'-di-N-formyl gentamicin B is triformylisepamicin, compound IV.

The protecting groups are removed from the Compound IV by hydrolysis according to the following reaction scheme.

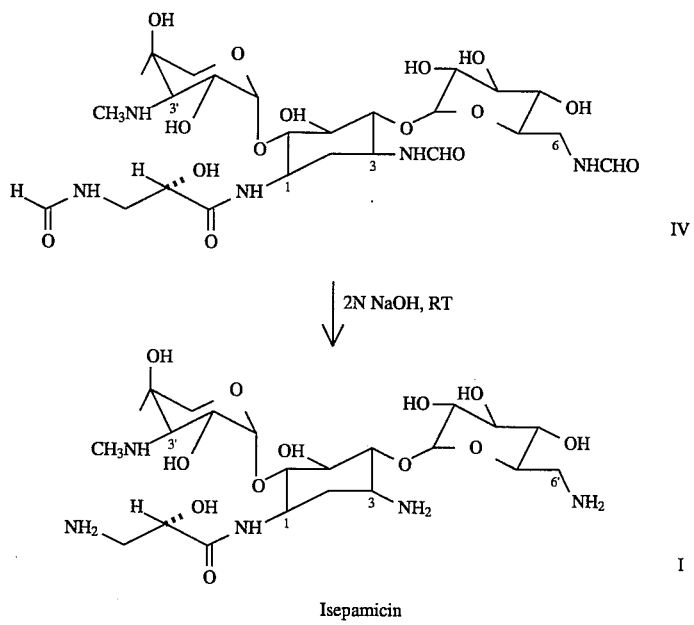

Isepamicin

Prior to deblocking Compound IV, the solvent is removed from the reaction mixture. Although deblocking by hydrolysis is a conventional procedure the specificity for formyl group removal without removal of the isoserine side chain is unprecedented in the aminoglycoside field. It has been found that when the hydrolysis reaction is conducted by stirring overnight at room temperature, an excellent yield (88–90%) of desired product is obtained. The resulting hydrolysate is acidified to pH 6 with acid and isepamicin is obtained by isolation.

The following Examples are illustrative of a preferred mode of carrying out our invention but are not to be construed as limiting the scope thereof. Equivalents thereof will be obvious to one skilled in the art reading this application and said equivalents are contemplated as included within this invention. In the example HPLC means High Performance Liquid Chromatography; Amberlite IRC-50 is a weak cation ion exchange resin available from Rohm and Haas Company.

EXAMPLE 1

Preparation of 2-Formylmercaptobenzothiazo

To a dry three-necked 500 ml round bottom flask was added 80 ml of acetonitrile, 5.0 ml (0.133 mole) of formic acid and 18.1 g (0.266 mole) of sodium formate. The resulting suspension was cooled to 0°–5° C. and 14.6 ml (0.2 mole) of acetyl chloride was added slowly, while maintaining the temperature of the reaction mixture below 8° C. After the addition of acetyl chloride was complete, the reaction mixture was allowed to warm up to 18°–20° C. The completeness of the reaction was judged by $^1$H-NMR. To the heterogeneous mixture containing acetic formic anhydride, 60 ml of acetonitrile was added followed by 20 g (0.103 mole) of 2-mercaptobenzothiazole and the temperature was allowed to warm up to 32° C. and maintained at that temperature, while the progress of the reaction was monitored by HPLC at 10 minute intervals. The reaction was considered to be complete when ca. 4% of 2-mercaptobenzothiazole (by area %) remained unreacted or when its area % starts to increase due to decomposition of the product.

The reaction mixture was then quenched with 200 ml of ice-water and stirred for 2 minutes. The precipitated product was filtered, washed thoroughly with water (4×150 ml) and dried under vacuum until the water content of the solid is <0.08% to afford 21.4 g (98% pure by HPLC, 89% yield) of 2-formylmercaptobenzothiazole, m.p. 125°–130° C. (decomposition)

$^1$H-NMR (CDCl$_3$) w 7.36–7.44 (m,3H), 8.45–8.52 (m, 1H), 9.92 (S,1H).

EXAMPLE 2

Preparation of Zinc Pivaloate

To 250 ml of water, warmed to 60°–70° C., was added 56.1 gm (0.55 mole) of pivalic acid (trimethylacetic acid). Then 31.25 gm (0.25 mole) of zinc carbonate was added portionwise over a period of 10 to 15 minutes and then the temperature was raised to 96°–98° C. After agitating the reaction mixture for 1 hour, the mixture was cooled to 4° C. with an ice bath for 30 minutes and the suspension filtered. The filter cake was washed once with 75 ml cold water and 3×50 ml cold acetone. The resulting product was dried at 60° C. for 16 hours in a draft oven to yield 58 gm (87%) of zinc pivaloate.

EXAMPLE 3

3,6'-Di-N-formylgentamicin B

To 285 ml of dimethylsulfoxide and 285 ml of methylene chloride was added 34.0 g (127 mmole) of zinc pivaloate and 19 g of gentamicin B (purity 93.1%, 36.7 mmole). The resulting suspension was stirred for 10 to 15 minutes at room temperature to effect solution. To this solution was added 16.0 g of 2-formylmercaptobenzothiazole (81.9 mmole) and after five minutes an aliquot was taken for liquid chromatographic analysis of the ratio of the monoformyl/diformyl peaks. Two more small additions were made such that the eventual total charge was 16.95 g (86.8 mmole) to give a final peak ratio of 0.02, which was judged to be complete.

The reaction mixture was transferred to a 2 liter separatory funnel and 800 ml of water was added. The phases were separated, and the aqueous layer was re-extracted with a 30 ml portion of methylene chloride. The aqueous layer was then filtered thorough a small pad of celite to remove a haze of solids.

The filtrate was diluted with water to a final volume of 2 liters, and its pH was about 6 at this point. This aqueous solution was charged onto a column containing 800 ml of Amberlite IRC-50 resin which had been adjusted to a partial ammonium cycle. The product was eluted with 0.75N ammonium hydroxide; the fractions containing the product were pooled and concentrated to yield a solution, which was assayed by liquid chromatographic analysis and found to contain 17.9 g (90.5%) of 3,6'-di-N-formylgentamicin B. Mass spectrum m/e (%) (FAB/GLY-THIO) 539 (100, M$^+$+1), 511(9), 380(9), 350(4), 191(10), 190(5), 160(28).

$^1$H-NKR (400 MHz, D$_2$O; pH=9) w 1.25 (s, 3H, C-4"—CH$_3$), 2.57 (s, 3H, N—CH$_3$), 5.11 (d, J=4.02 Hz, 1H, anomeric), 5.38 (d, J=4.02 Hz, 1H, anomeric), 8.15 (s, 1H, N—CHO), 8.16 (s, 1H, N—CHO).

$^{13}$C-NMR (100 MHZ, D$_2$O; pH=9) w 51.36(C-1), 47.8(C-3), 38.96(C-6'), 64.5(C-3"), 37.01(N—CH$_3$), 22.22(C-4"—CH$_3$), 165.47 (N—CHO), 164.76(N—CHO).

EXAMPLE 4

Preparation of N,O-Diformyl-(S)-Isoserine

To a one liter round bottom flask containing 50 g of (S)-isoserine (0.476 mole) and 62.5 ml of formic acid was added in 30 min. a freshly prepared acetic formic anhydride solution (5 eq.) at 0°–5° C. After examining the completion of reaction by H$^1$-NMR (approx. 2 hrs), the mixture was concentrated under vacuum at 40° C. to half of the original volume. 250 ml of isopropanol was added slowly with simultaneous cooling to effect crystallization. The slurry was stirred at 0° C. for one hour. The product, N,O-diformyl-(S)-isoserine, was filtered and washed with isopropanol. This afforded 64 g of N,O-diformyl-(S)-isoserine; 84% yield; m.p. 139.5°–141.5°; [a]$_D^{20}$: –38° (1%, MeOH). 6 * Acetic formic anhydride was prepared by adding acetyl chloride to 1.2 eq. of sodium formate (anhydrous, micronized) in anhydrous acetonitrile (the concentration of sodium formate/CH$_3$CN can be as high as 50%) at 0°–5° C. The reaction takes 2 hours to complete. The precipitate was filtered, the filtrate was used as is in the above reaction. Some carbon monoxide is evolved from this mixture, depending on the temperature. Reasonable stability was observed at 0° for one month.

$^1$H-NMR (D$_2$O) w 3.8 (dd, 1H, J=14.6, 4.4 Hz), 3.91 (dd, 1H, J=14.6, 5.5 Hz), 5.38 (dd, 1H, J=5.5, 4.4 Hz), 8.15 (s, 1H), 8.27 (s, 1H).

EXAMPLE 5

Preparation of N-Phthaloyl-(S)-Isoserine

To a stirred suspension of 15.75 g (150 mmole) of (S)-isoserine and 22.2 g (150 mmole) of phthalic anhydride in 600 ml of toluene:dimethylformamide (3:1), was added 2.1 ml (15 mole) of triethylamine. The suspension was heated to reflux and the water generated was removed using a Dean-Stark condenser. No additional water separated after two (2) hours at reflux. The solvent was evaporated to a final volume of approximately 100 ml. The reaction mixture was cooled, diluted with ice-water and acidified with 2N hydrochloric acid to afford a precipitate. The product was filtered, washed with ice-water and dried under vacuum to yield 30.4 g (86%) of N-phthaloyl -(S)-isoserine; m.p. 227°–228° C; $[a]_D^{20}$: +10 (1%, DMF). $^1$H-NMR (DMSO-d$_6$) w 3.76 (dd, 1H, J=13.46, 7.69 Hz), 3.84 (dd, 1H, J=13.46, 5.77 Hz), 4.3 (dd, 1H, J=7.69, 5.77 Hz), 7.77–7.89 (m, 4H).

EXAMPLE 6

Preparation of N-trifluoroacetyl-S-isoserine

To a stirred solution of sodium methoxide in methanol, 11 ml (1 eq., 24.8% w/w solution) was added 5 g of (S)-isoserine. The mixture was stirred at room temperature for 15 minutes until a homogeneous solution was obtained. Ethyltrifluoroacetate, 7 ml (1.25 q.) was added. The mixture was stirred for 30 minutes after the addition. The completeness of the reaction was monitored by $^1$H-NMR. The mixture was concentrated under reduced pressure to as low a volume as possible. To the residue 50 ml ethylacetate was added. The mixture was cooled to 0°–5° C., 25 ml of 2N HCl (1 eq.) was added, followed by 5 g of solid sodium chloride. The organic layer was separated. The aqueous layer was reextracted with 50 ml of ethylacetate. The combined organic extracts were dried (over 5 g of anhydrous magnesium sulfate), filtered and concentrated under reduced pressure to 20 ml. To it 50 ml heptane was added with stirring in an ice-bath for 30 minutes. The product was filtered and dried to yield 8.86 g (93%) of N-trifluoroacetyl-(S)-isoserine; m.p. 142°–143° C.; $[a]_D^{20}$: +12.4 (1%, H$_2$O); $^1$H-NMR (D$_2$O) w 3.78 (d, 2H, J=5.48 Hz), 4.53 (t, 1H, J=5.48 Hz).

EXAMPLE 7

Preparation of Isepamicin

The following methods illustrate the preparation of Isepamicin.

Method A:

A stock solution of N-formyl-(S)-isoserine was prepared by stirring 20 g (124.2 mmoles) of N,O-diformyl-(S)-isoserine in a mixture of methanol (85 ml) and pyridine (15 ml, 1.5 equiv.) at room temperature for 14–16 hrs. The completion of the reaction was judged by $^1$HNMR.

In a separate flask, 20 g of aq. concentrate (4.424 g active, 8.2 mole) of 3,6'-diformyl gentamicin B and 1.26 g (8.26 mmole) of 1-N-hydroxybenzotriazole monohydrate were dissolved in 40 ml of methanol. To the stirred mixture the above N-formyl-(S)-isoserine solution in methanol (22.2 ml 24.4 mmoles, 3 equiv.) and a solution of dicyclohexyl carbodiimide (5 g, 24.3 mole, 3 equiv.) in 20 ml of methanol were added simultaneously over a period of 40 min. The mixture was stirred for 15 mins. after the addition was complete. The progress of the reaction was monitored by either HPLC or by TLC. The solvents were then removed under reduced pressure, and the product, triformylisepamicin, was hydrolysed by stirring at room temperature for 16 hrs. with 90 ml of 2N NaOH. The reaction mixture was neutralised to pH=6 with acid, filtered and the filtrate was diluted to a precise volume of 1000 ml. External standard HPLC assay of this solution indicated an 89% yield of isepamicin (4.17 g, 7.3 mole).

Method B:

A solution was prepared by dissolving 1.156 g (96.6% pure, 2.07 mole) of 3,6'-di-N-formylgentamicin B, 800 mg (1.7 eq.) of N-phthaloylisoserine and 365 mg (1.2 eq.) of N-hydroxybenztriazole monohydrate in 40 ml of methanol. To this solution was added 700 mg (1.7 eq.) of dicyclohexylcarbodiimide. The reaction was stirred at room temperature for one hour and 160 mg of N-phthaloyl-(S)-isoserine and 140 mg of dicyclohexylcarbodiimide was added and the reaction was allowed to stir at room temperature for approximately three (3) hours. The progress of the reaction was monitored by TLC. The solvent was removed by evaporation and the residue taken up in 50 ml ethanol and 5 ml water. The protecting groups were removed by treating the resulting mixture with 6.0 ml (85%) hydrazine hydrate. The reaction was heated at 85°–90° C. under nitrogen for 14 hours. External standard HPLC assay of the reaction indicated a yield of 89% (1.05 g, 1.85 mole) isepamicin.

Method C:

To 48.9 g of aq. concentrate (8.45 g active, 15.7 mmole) of 3,6'-diformylgentamicin B, 2.4 g (15.7 mmole) of 1-N-hydroxybenzotriazole monohydrate was added followed by 80 ml of methanol. To the stirred mixture, 9.5 g (47.3 mmole, 3 equiv.) of N-trifluoroacetyl-(S)-isoserine in 40 ml of methanol and 9.7 g (47.1 mmole, 3 equiv.) of dicyclohexyl carbodiimide in 40 ml of methanol were added simultaneously over a period of 40 min. The mixture was stirred for 15 min. after the addition was complete. The progress of the reaction was monitored by either HPLC or TLC. The solvents were then removed under reduced pressure, and the product was hydrolysed by stirring with 170 ml of 2N NaOH at room temperature for 16 hrs. The reaction mixture was neutralised to pH=6 with acid, filtered and the filtrate was diluted to a precise volume of 1000 ml. External standard HPLC assay of the solution indicated an 88% yield of isepamicin (7.84 g, 13.8 mmole).

We claim:

1. The compound 2-formylmercaptobenzothiazole.

* * * * *